US008296084B1

(12) United States Patent
Hickling

(10) Patent No.: US 8,296,084 B1
(45) Date of Patent: Oct. 23, 2012

(54) NON-CONTACT, FOCUSED, ULTRASONIC PROBES FOR VIBROMETRY, GAUGING, CONDITION MONITORING AND FEEDBACK CONTROL OF ROBOTS

(76) Inventor: Robert Hickling, Huntington Woods, MI (US)

(*) Notice: Subject to any disclaimer, the term of this patent is extended or adjusted under 35 U.S.C. 154(b) by 0 days.

(21) Appl. No.: 13/374,828

(22) Filed: Jan. 17, 2012

(51) Int. Cl.
G01B 17/00 (2006.01)
G01H 1/00 (2006.01)
G06F 19/00 (2011.01)

(52) U.S. Cl. ......... 702/56; 73/602; 73/865.8; 73/866.3; 702/35; 702/39; 702/187; 708/200

(58) Field of Classification Search ............ 33/501, 33/503, 505, 533; 73/432.1, 570, 577, 578, 73/584, 587, 596, 602, 618, 619, 627, 629, 73/632, 642, 865.8, 866, 866.3; 181/139, 181/175, 176; 381/150, 337; 702/1, 33, 702/34, 35, 39, 56, 127, 155, 167, 187, 189; 708/100, 105, 200
See application file for complete search history.

(56) References Cited

U.S. PATENT DOCUMENTS

| | | | | |
|---|---|---|---|---|
| 2,525,873 A * | 10/1950 | De Lano, Jr. | | 73/606 |
| 2,592,222 A * | 4/1952 | Williams | | 73/606 |
| 2,779,880 A * | 1/1957 | Malherbe | | 310/335 |
| 2,838,930 A * | 6/1958 | Krautkramer et al. | | 73/629 |
| 3,192,418 A * | 6/1965 | Sansom | | 310/335 |
| 4,364,264 A * | 12/1982 | Re Fiorentin | | 73/105 |
| 4,580,451 A * | 4/1986 | Miwa et al. | | 73/626 |
| 4,655,083 A * | 4/1987 | Chubachi | | 73/606 |
| 5,024,093 A * | 6/1991 | Sasaki et al. | | 73/633 |
| 5,036,707 A * | 8/1991 | Paciej et al. | | 73/637 |
| 5,517,994 A * | 5/1996 | Burke et al. | | 600/437 |
| 5,922,961 A * | 7/1999 | Hsu et al. | | 73/606 |
| 6,027,449 A * | 2/2000 | Mazess et al. | | 600/449 |
| 6,081,481 A | 6/2000 | Sabatier et al. | | |
| 6,364,837 B1 * | 4/2002 | Mazess et al. | | 600/449 |
| 6,425,865 B1 * | 7/2002 | Salcudean et al. | | 600/437 |
| 6,938,488 B2 * | 9/2005 | Diaz et al. | | 73/597 |
| 7,751,281 B1 | 7/2010 | Hickling | | |
| 2004/0035208 A1 * | 2/2004 | Diaz et al. | | 73/597 |
| 2010/0041991 A1 * | 2/2010 | Roundhill | | 600/443 |
| 2010/0262008 A1 * | 10/2010 | Roundhill | | 600/453 |

OTHER PUBLICATIONS

J.M. Buckley, "An Introduction to Eddy-Current Testing, Theory and Technology" C\My Documents\Joe Work\TEKINTRO.DOC (2011).
M. Johannsmann, G. Siegmund and M. Pineda, "Targeting the limits of Laser Doppler Vibrometry", Proc. International Disc Drive Equip.& Mat. Assoc. (2005).
J. V. Dahlmann and R. Hickling, "Focused ultrasound to inspect locking keys in engine valves", Sensors, Journ. of Machine Perception, 7, 27-38, (1990).

* cited by examiner

Primary Examiner — Edward Cosimano
(74) Attorney, Agent, or Firm — Reising Ethington P.C.

(57) ABSTRACT

Method and apparatus for vibrometry, gauging, condition monitoring and feedback control of robots, using one or more ultrasonic probes (100) that are non-contact and form a focused beam. The ultrasonic probe is driven by a pulser-receiver (120) controlled by a computer. The probe has a substantially spherical transducer surface (75) that forms the focused beam within a gas or a liquid. The curvature of the transducer surface determines the focal length (25) and the extent of the focal region (50) of the beam. For greatest lateral accuracy, measurements are made within the focal length, where beam is narrowest. Diameter (80) of the probe determines the size of the beam, which can be chosen to satisfy a particular application. The focused beam has acoustic depth of field (85), which is the furthest distance from the probe to a surface (90) that can return a measurable echo to a pulse emitted by the probe.

15 Claims, 6 Drawing Sheets

NON-CONTACT, FOCUSED, ULTRASONIC PROBES FOR VIBROMETRY, GAUGING, CONDITION MONITORING AND FEEDBACK CONTROL OF ROBOTS

TECHNICAL FIELD

This invention relates to vibrometry, gauging, condition monitoring and feed back control of robots, using non-contact, focused, ultrasonic probes.

BACKGROUND OF THE INVENTION

Vibrometry

Non-contact, focused, ultrasonic vibrometry has been described in
1. R. Hickling "Detection of Buried Objects using an Array of Non-Contact, Ultrasonic Vibrometers", U.S. Pat. No. 7,751,281 Jul. 6, 2010.

Vibration is often measured using accelerometers securely attached to a surface. However accelerometers cannot be used on rotating shafts and other moving parts, or where the measurement location is constantly changing. In such situations, eddy-current, laser and other methods are used.

Eddy-current methods are described in
2. J. M. Buckley "An Introduction to Eddy-Current Testing, Theory and Technology" C:\My Documents\Joe Work\TEKINTRO.DOC (2011).

Eddy-current probes have several drawbacks. They can be used only with electrically conducting surfaces and have to be positioned very precisely, at short ranges of a few millimeters. Also they can lack lateral resolution and are relatively expensive. In contrast, the beams of non-contact, focused, ultrasonic probes have a focal length and an acoustic depth of field that does not require precise positioning. They can be used in any gas or liquid. Also they can be used for any solid or liquid surface. The small spot size in the focal length of the beam provides good lateral resolution.

The use of lasers principally involves laser-Doppler vibrometry (LDV), such as described in
3. J. M. Sabatier and K. E. Gilbert, "Method of detecting buried objects by measuring seismic vibrations by coupling with a remote source of sound", U.S. Pat. No. 6,081,481, Jun. 27, (2000).

A more general account of LDVs is given in
4. M. Johannsmann, G. Siegmund and M. Pineda, "Targeting the limits of Laser Doppler Vibrometry", Proceedings, International Disk Drive Equipment and Materials Association, (2005).

Drawbacks of LDVs are: (a) cost; (b) an optically reflecting surface is generally required and (c) interference can occur from background vibration. In contrast, non-contact, focused, ultrasonic probes are cheaper, more rugged and do not require an optically reflecting surface. The probes can be used in liquids as well as in gases. Interference from background vibration is generally minimal.

Gauging and Inspection

Most non-contact gauging and inspection devices use optics. Various techniques are employed such as shadow projection, pattern recognition, interferometry and triangulation. In general these provide only two-dimensional information and lack depth perception. Triangulation can provide depth perception but it has difficulty with irregular surfaces. Eddy-current devices can perform non-contact gauging but only at short ranges of a few millimeters. In contrast, the beams of focused ultrasonic probes have a longer range and have little difficulty with irregular surfaces, as shown in
5. V. Dahlmann and R. Hickling, "Focused Ultrasound to Inspect Locking Keys in Engine Valves", Sensors, Journal of Machine Perception, 7, 27-38, (1990).

Non-contact, focused, ultrasonic probes can also be used for feedback control of robots.

Condition Monitoring

There are many situations where continuously operating, mechanical systems have to be monitored to detect wear and prevent a breakdown. Examples of such systems are: (a) heavy rotating machinery used for power generation and in ships; (b) railroads; (c) water and gas pipelines; (d) pipelines in the petrochemical, pulp, paper industries and (e) nuclear reactors. Non-contact, focused, ultrasonic probes are ideal for condition monitoring in these applications.

Robot Guidance

Non-contact, focused, ultrasonic probes can be used for feedback control of robots moving in a manner and direction not previously planned.

SUMMARY OF THE INVENTION

The present invention includes and utilizes an acoustic apparatus for vibrometry, gauging, condition monitoring and feedback control of robots. It includes one or more ultrasonic probes that are non-contact and focused, each probe connected to a puller-receiver that is operated by a computer. The computer is also used for data storage. Data and information from the computer are presented on a display device. An ultrasonic probe has a substantially spherical transducer that forms a focused beam within a gas or a liquid. The radius of the transducer surface determines the focal length and the extent of the focal region. For lateral accuracy, measurements are made within the focal region where the focused beam is narrowest. The diameter of the probe determines the dimensions of the beam and can be chosen for a particular application.

When the non-contact, focused, ultrasonic probe is used as a vibrometer, it emits pulses at a much faster rate, typically a few hundred times or more, greater than the frequency of a surface whose vibrations are being measured. This permits the pulser-receiver and computer to follow the motion of the vibrating surface and present the information on the display device.

In addition the probes can be used to gauge the correct position, condition and assembly of objects on a production line. Also they can be used to monitor the condition of a mechanical system that operates continuously over an extended time, to determine wear and to detect impending breakage and malfunction. In addition, within the acoustic depth of field, a probe can determine the perpendicular distance to a flat surface. It can also be used for feedback control of a robot.

BRIEF DESCRIPTION OF THE DRAWINGS

In the drawings:

FIG. 7A illustrates positioning an object: FIG. 7B illustrates leveling a plate; FIG. 7C illustrates measuring the warpage and flatness of a plate; FIG. 7D illustrates measuring the thickness of a plate with two opposing non-contact focused, ultrasonic probes.

DESCRIPTION OF THE PREFERRED EMBODIMENT

Figure 1:
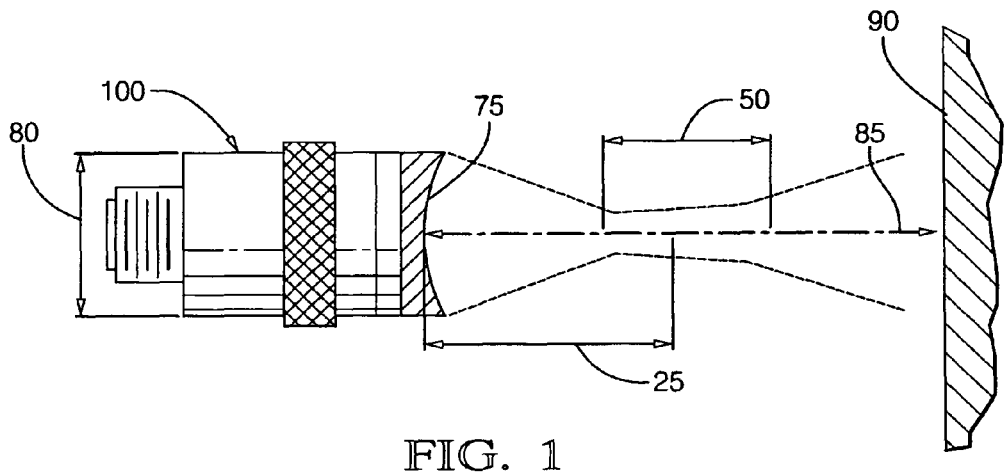
FIG. 1 shows the focused beam of a non-contact, ultrasonic probe.
Figure 2:
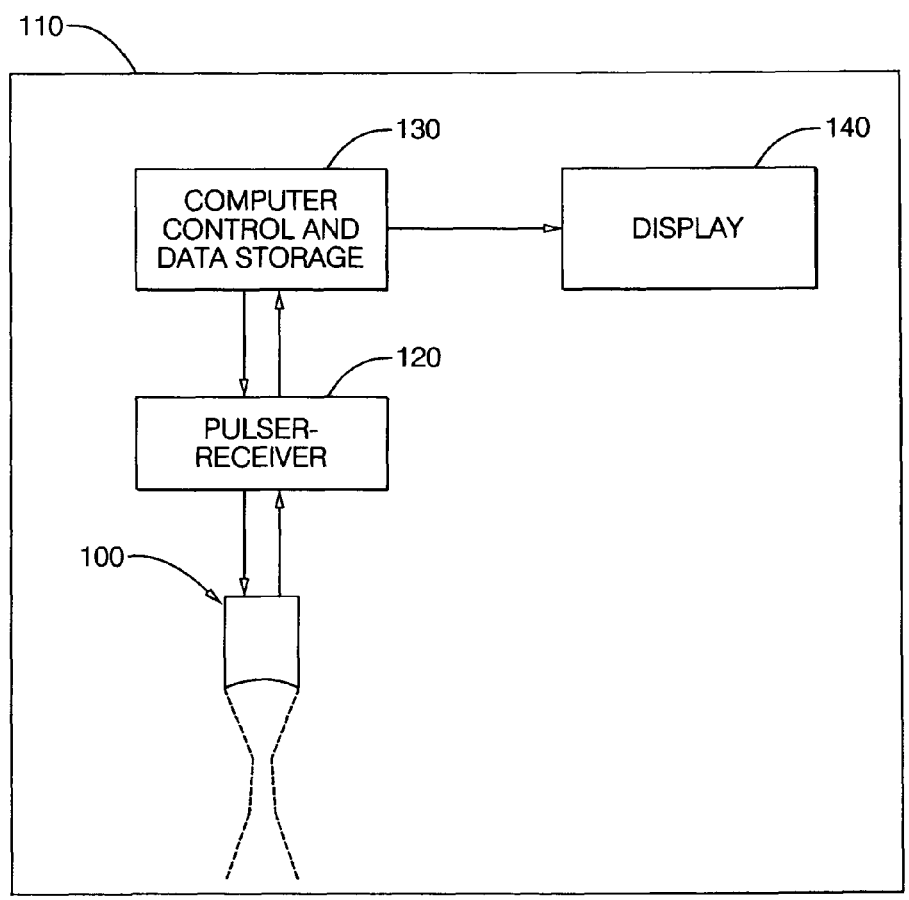
FIG. 2 is a block diagram of the operating system for a non-contact, focused, ultrasonic probe.

FIG. 1 shows the beam shape of a non-contact, focused, ultrasonic probe 100. The probe has a substantially spherical transducer surface 75 that forms a beam within a gas or a liquid. The curvature 75 of the transducer surface determines the focal length 25 and the extent of the focal region 50 of the beam. For greatest lateral accuracy, measurements are made within the focal length 25, where the beam is narrowest. The diameter 80 of the probe determines the size of the beam, which can be chosen for a particular requirement. The acoustic depth of field 85 is the furthest distance from the probe to a surface 90, where the surface 90 is capable of returning a measurable echo to a pulse emitted by the probe. FIG. 2 is a schematic of the system 110 that operates a non-contact, focused, ultrasonic probe. It consists of pulser-receiver 120 controlled by a computer 130. The computer is also used for data storage. Results from the system 110 are displayed using a device 140. Ultrasonic probes in air and pulser-receivers were originally manufactured by Harisonics Inc. and Staveley Sensors Inc. These companies were acquired by Olympus NDT, who no longer provides air transducers.

Figure 3:
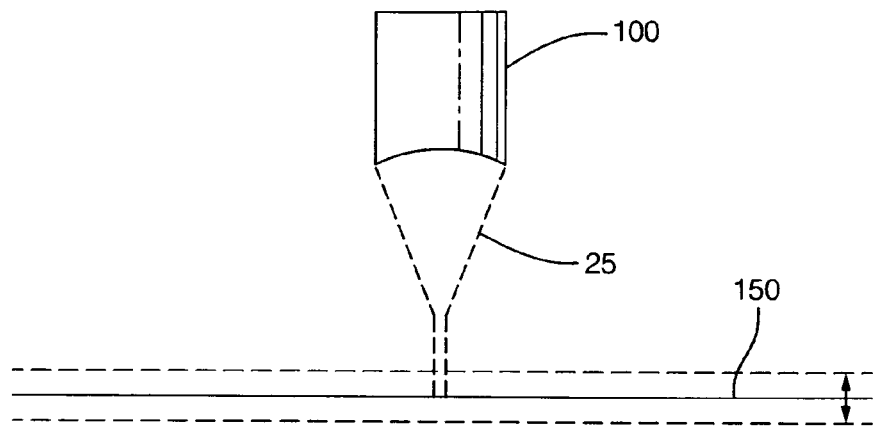
FIG. 3 is a diagram showing the measurement of surface vibrations using a non-contact focused, ultrasonic probe.
Figure 4:
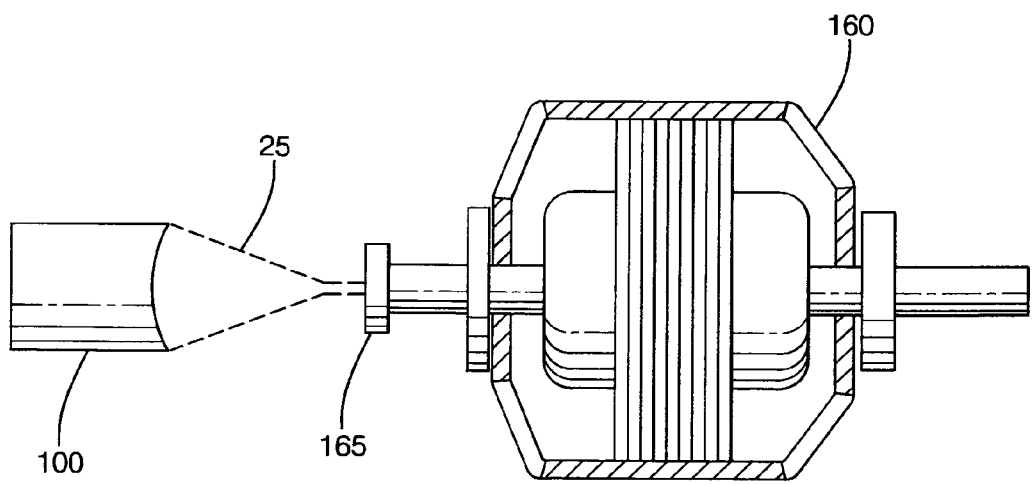
FIG. 4 is a cross-sectional drawing of a non-contact, focused, ultrasonic probe measuring the axial vibration at the end of the shaft of a small electric motor.
Figure 5:
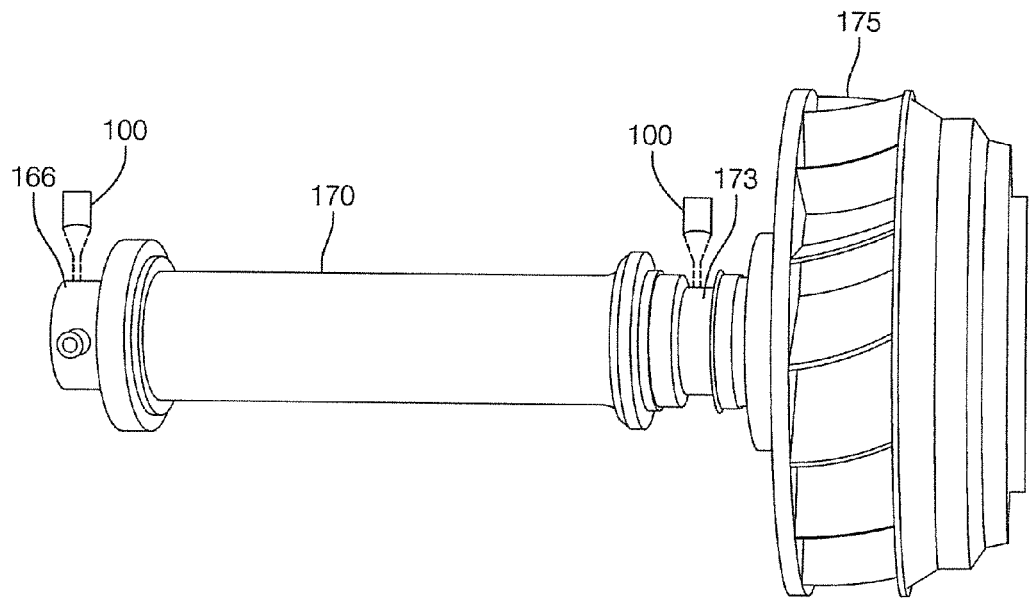
FIG. 5 shows two possible locations for non-contact, focused, ultrasonic probes for condition monitoring of the radial vibrations of the shaft of a steam turbine.
Figure 6:
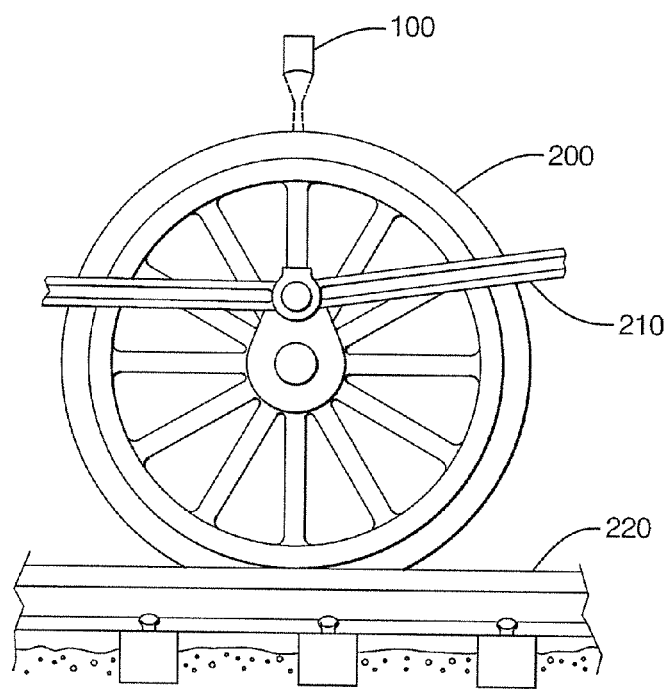
FIG. 6 Condition monitoring of the vibration of a train wheel on a railroad track

Use of the probe 100 as a vibrometer is illustrated in FIG. 3. Measurements are usually made within the focal length of the probe. The pulser-receiver 120 drives the probe at a frequency much greater than the frequency of the vibrating surface 150, thus permitting the system 110 to follow and display the motion of the surface 150 in detail. FIG. 4 is a simple example of non-contact vibrometry showing measurement of the axial vibration of the end 165 of the shaft of a small electric motor 160. Larger-scale applications are shown in FIGS. 5 and 6. FIG. 5 is a shaft 170 driven by steam turbine 175, such as is used in power plants and ships. Non-contact probes located at 166 and 173 measure the radial vibrations of the shaft to detect wear and an impending malfunction or breakage of the shaft. FIG. 6 shows the wheel of a train, with an outer rim 200 running on a railroad track 220 and driven by linkage 210. A probe 100 monitors the vibration of the wheel and track to detect possible misalignment and malfunction. Non-contact, focused, ultrasonic probes can be used to monitor the drive mechanisms of electric and diesel-electric locomotives. In general a non-contact, focused, ultrasonic probe can be used for the condition monitoring of any mechanical device, such as an automobile, airplane or a manufacturing system.

Figure 7A:
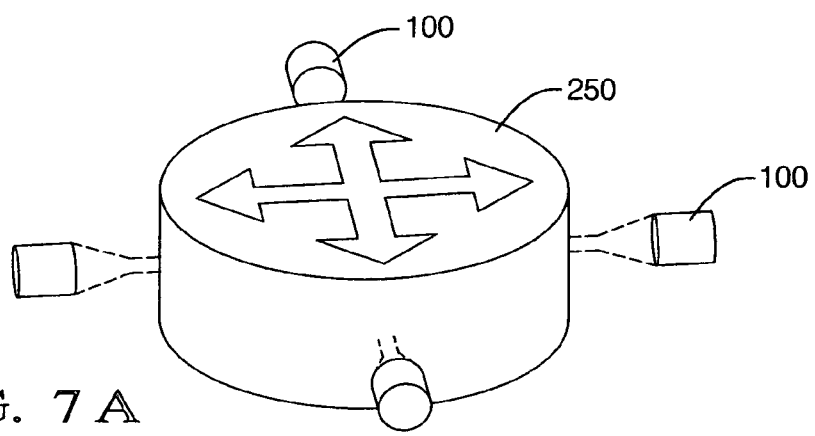
FIGS. 7A, FIG. 7B, FIG. 7C and FIG. 7D illustrate examples of gauging on a production line as follows.
Figure 7B:
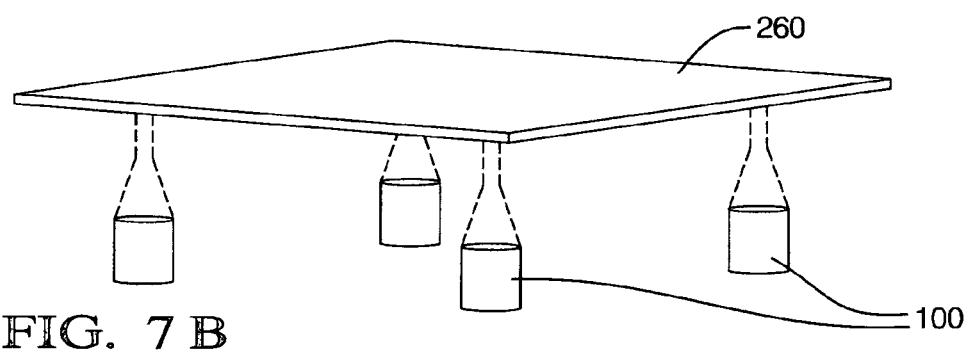
Figure 7C:
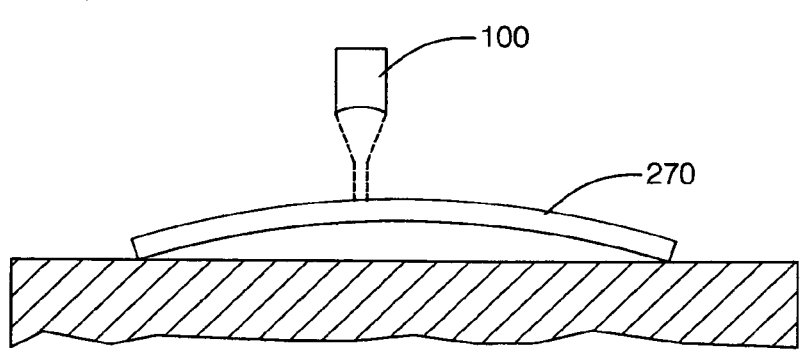
Figure 7D:
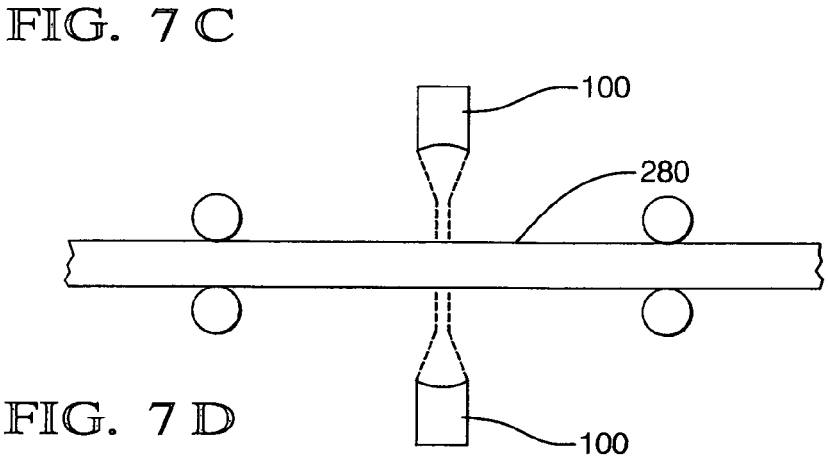

FIGS. 7A, 7B, 7C and 7D show the use of non-contact, focused ultrasonic probes for positioning and gauging. FIG. 7A shows the positioning of an object 250; FIG. 7B shows the leveling of a plate 260; FIG. 7C shows detection of warpage in a plate 270 moving under the probe 100 and FIG. 7D shows measurement of the thickness of a plate 280 between two directly opposite probes 100.

Figure 8:
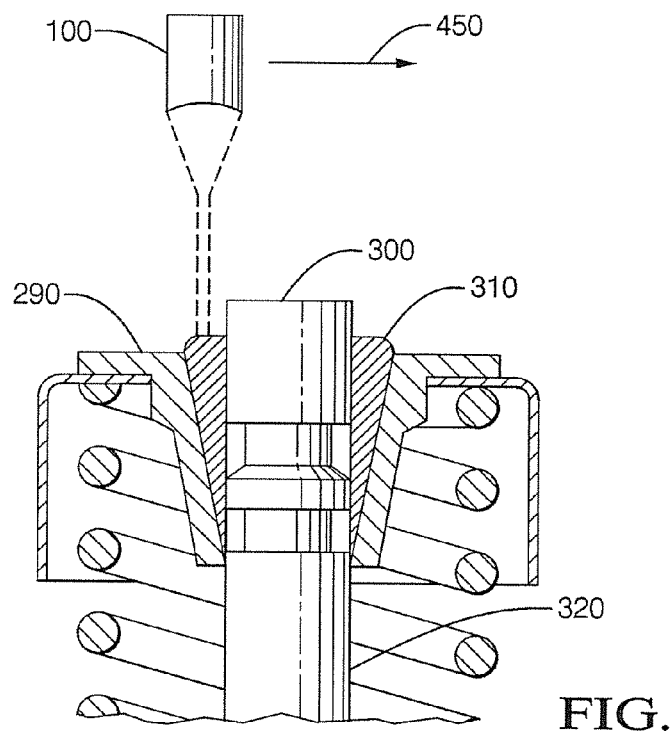
FIG. 8 is a fragmentary segment illustrating checking for missing and out-of-position locking keys and other components in an engine valve, on a production line.
Figure 9:
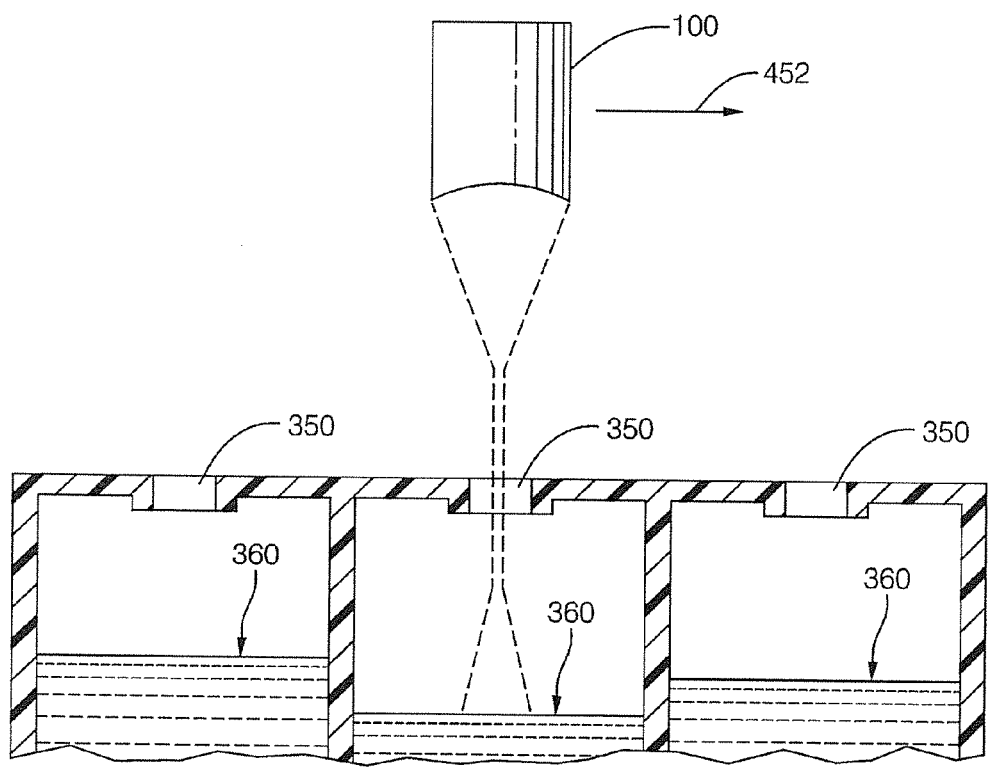
FIG. 9 is a fragmentary segment illustrating checking the acid levels in the compartments of a battery on a production line.
Figure 10:
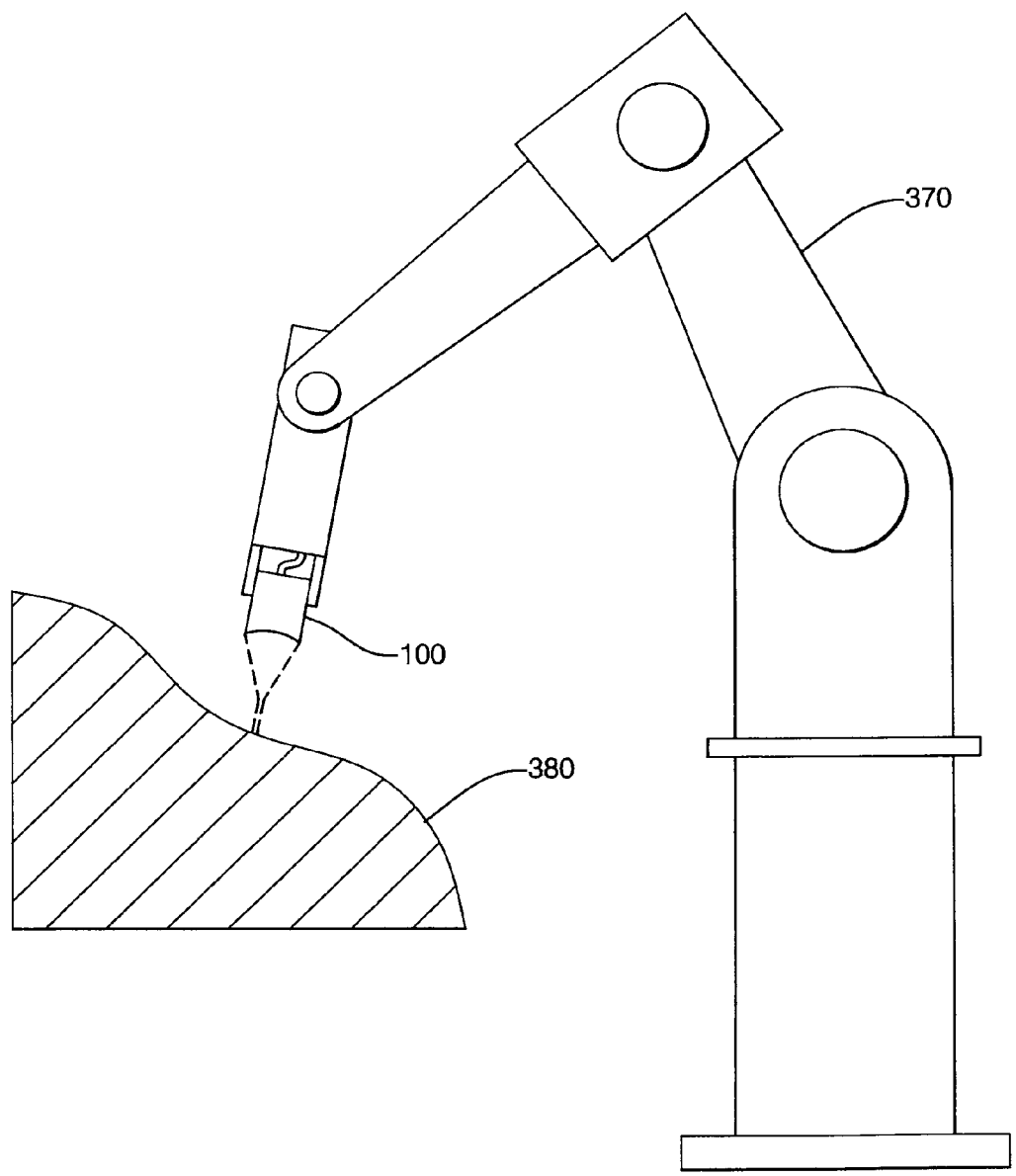
FIG. 10 is a fragmentary segment illustrating scanning an arbitrary surface, using a non-contact, focused, ultrasonic probe that provides feedback control for a robot arm.

FIG. 8 shows a probe scanning the top of an engine valve 300 on a production line that may move in a direction indicated by arrow 450 in order to detect missing and out-of-position locking keys 310 or other components, such as the valve cap 290 and stem 320. Currently this task is performed using computer vision, which lacks the depth perception of a non-contact, focused, ultrasonic probe. FIG. 9 shows a probe at a fixed height measuring the acid level 360 in the compartments of a battery on a production line that may move in a direction indicated by arrow 452. The narrow focal section 50 of the beam enters through the fill hole 350. The beam then expands within the acoustic depth of field 85, returning an echo from the acid level 360 to the pulser-receiver. The elapsed time between the pulse emitted by the probe and the received echo determines the acid level in each compartment. Currently in industry, the acid level is determined as follows. The production line is halted and a set of fiber-optic dipsticks is inserted through the fill holes to determine the acid levels in the compartments. Obviously it would be more advantageous not to halt the production line. As a final example, FIG. 10 shows a non-contact, focused, ultrasonic probe 100 attached to a robot arm 370. The probe is determining the shape of an arbitrary surface 380 using feedback control of the arm 370. The applications described here are for probes ii air. The probes could similarly be used in gases other than air and in liquids.

While the invention has been described by reference to certain preferred embodiments, it should be understood that numerous changes could be made within the spirit and scope of the inventive concepts described. Accordingly it is intended that the invention not be limited to the disclosed embodiments, but that it have the full scope permitted by the language of the following claims:

I claim:

1. An apparatus for vibrometry, gauging, condition monitoring and feedback control of robots, comprising:
    an ultrasonic probe that is non-contact with respect to an object and forms a focused beam onto said object through an uncontained ambient fluid medium between said probe and object;
    a pulser-receiver connected to the ultrasonic probe;
    a computer for operating the pulser-receiver and for data storage;
    computer programs for vibrometry, gauging or condition monitoring from data received from said ultrasonic probe; and
    a display device for presenting vibrometry, gauging or condition monitoring information and data from the computer that is based on data received from said ultrasonic probe.

2. The invention as in claim 1 wherein said ultrasonic probe is used as a vibrometer, by emitting pulses at a much faster rate, typically a few hundred times faster or more, than the frequency of a surface whose vibrations are being measured, such that said computer follows the vibratory motion of said surface and presents this information on said display device.

3. The invention as in claim 1 wherein said ultrasonic probe is used to gauge the correct position, condition and assembly of said object.

4. The invention as in claim 1 wherein said ultrasonic probe monitors the condition of a mechanical system that operates continuously over extended periods of time, in order to detect the wear and any impending breakage or malfunction of the system.

5. The invention as in claim 1 wherein the fluid medium is either a gas or a liquid.

6. The invention as in claim 5 wherein the diameter of said ultrasonic probe is selected to determine the dimensions of said focused beam.

7. The invention as in claim 1 wherein said ultrasonic probe determines the perpendicular distance from said ultrasonic probe to a flat section of surface, within the acoustic depth of field of said ultrasonic probe.

8. The invention as in claim 7 wherein the beam of said ultrasonic probe is formed in air or other gas and said flat section of surface is a liquid or a solid or a different gas.

9. The invention as in claim 1 wherein said ultrasonic probe has a substantially spherical transducer surface that forms said focused beam within said fluid medium.

10. The invention as in claim 9 wherein the curvature of the transducer surface determines the focal length and extent of the focal region of said focused beam.

11. The invention as in claim 10 wherein measurements can be made in the focal region where the focused beam is narrowest and lateral accuracy is greatest.

12. An apparatus for vibrometry, gauging, condition monitoring and feedback control of robots, comprising:
   an ultrasonic probe that is non-contact and forms a focused beam in a fluid medium;
   a pulser-receiver connected to the ultrasonic probe;
   a computer for operating the pulser-receiver and for data storage;
   computer programs for vibrometry, gauging or condition monitoring from data received from said ultrasonic probe;
   a display device for presenting information and data from the computer; and
   wherein said ultrasonic probe is used for feedback control of a robot.

13. A method for vibrometry, gauging, condition monitoring or feedback control of a robot, using an ultrasonic probe comprising the steps of:
   said ultrasonic probe being non-contact with respect to an object and emitting pulses in either an uncontained gas or liquid, in the form of a focused beam with a narrow focal length of finite extent and known depth of field, said focus beam passing through said uncontained gas or liquid from said probe to said object;
   said ultrasonic probe being driven by a pulser-receiver;
   the pulser-receiver being controlled by a computer;
   said pulser-receiver receiving echoes from said pulses from a flat section of the surface of gas or liquid that differs from the medium in which said pulses are transmitted and sending received data regarding said echoes to said computer for vibrometry, gauging, condition monitoring or feedback control of said robot; and
   the computer and said pulser-receiver providing an output relating to vibrometry, gauging, condition monitoring or feedback for a robot being presented on a display device.

14. The method as defined in claim 13 wherein said vibrometry, gauging, condition monitoring and feedback control of a robot, are within the depth of field of said ultrasonic probes.

15. The method as defined in claim 13 wherein said ultrasonic probes are used as a vibrometer by emitting pulses at a much faster rate, typically a few hundred or more times faster, than the frequency of a vibrating surface, thus permitting said computer to determine the vibratory motion of said surface and to present this information on said display device.

* * * * *